US00PP08542P

United States Patent [19]

Ortega

[11] Patent Number: Plant 8,542

[45] Date of Patent: Jan. 18, 1994

[54] ROSE PLANT LAUREN ELIZABETH

[76] Inventor: Carlos L. Ortega, 268 Sparrow Dr., Hercules, Calif. 94547

[21] Appl. No.: 820,136

[22] Filed: Jan. 13, 1992

[51] Int. Cl.[5] ..... A01H 5/00

[52] U.S. Cl. ..... Plt./11

[58] Field of Search ..... Plt. 11, 18, 7.1, 9, Plt. 22, 26

*Primary Examiner*—Howard J. Locker

*Assistant Examiner*—E. F. McElwain

[57] ABSTRACT

A new rose variety of the hybrid tea class characterized by having large, well formed and very fragrant light lavender flowers.

The present invention relates to a new and distinctive variety of rose plant of the hybrid tea class, which was originated by my crossing 'Moonlight', as the seed parent, with an unnamed seedling (Paul's Pink×Sterling Silver), as the pollen parent.

Among the novel characteristics possessed by the new variety which distinguish it from:

(a) Its parents and all other varieties of which I am aware are:

1. A plant which produces very large leaves;
2. A light lavender flower which darkens as it matures and produces a very strong, sweet and fruity fragrance;
3. A very rapid flowering cycle;
4. Good keeping quality as a cut flower, lasting 7–9 days in the vase after harvest and 9 to 13 days on the plant;
5. A very tall upright plant with few prickles.

(b) Seed parent: hybrid tea, white, very tall.

(c) Pollen parent: hybrid tea, lavender, weak growth.

Asexual reproduction of the new rose variety by grafting, as performed at Richmond, Calif. shows that the aforementioned characteristics and distinctions come true to form and are established and transmitted through successive propagations.

The accompanying drawing shows typical specimens of the vegetative growth and flowers of the new variety in different stages of development. The specimens are depicted in color as nearly true as it is reasonably possible to make them in a color illustration of this type.

The following is a detailed description of my new variety, with color terminology in accordance with The Royal Horicultural Society Colour Chart (R.H.S.C.C.). The terminology used in the color description herein refers to plate numbers in the aforementioned color chart, e.g. "53A" is plate 53A of The Royal Horticultural Society Colour Chart.

American Rose Society Registration commercial appellation:

'LAUREN ELIZABETH'

Parentage: Seedling

*Seed parent.*—'Moonlight', U.S. Plant Pat. No. 5,743.

*Pollen parent.*—Unnamed Cultiver (Paul's Pink, U.S. Plant Pat. No. 4,613×Sterling Silver, U.S. Plant Pat. No. 1,433).

Class: Hybrid tea

The following observations are made of specimens grown under glass in Contra Costa County, Calif.

FLOWER

Blooming Habit

A. Bud:

1. *Size.*—Medium.
2. *Form.*—Long, pointed ovoid.
3. *Sepals.*—to 5 cm in length; having 2 to 3 cm extension beyond bud; no serration shown on sepal edges. Generally, 3 out of 5 sepals show 1 to 3 appendages on each side of 2–8 mm length, smooth matting on inner surface of sepals. Smooth on outer surface.
4. *Peduncle.*—Length 10 cm; Surface-smooth to slightly prickly. Strength-stiff, slender and straight. Color 143 B.
5. *Color.*—When sepals first divide — outside petals 75C shading to 75B; areas lastly covered by sepals are close to 75D.

B. Bloom:

1. *Size.*—Average when open — 12 cm.
2. *Borne.*—Mostly single.
3. *Form.*—When first open — high center; flattens and all petals curl in maturity.
4. *Petalage.*—Average number — 25–30.
5. *Color.*—The upper side of the petal is 75B. The outer edge then fades to 75D with maturity. The reverse side is 62C. Color at base of petal is close to 155A. Surface aging of upper petal side is 186D. Reverse side ages to 76D.

C. Petals:

1. *Textures.*—Thin
2. *Shape.*—Round to oval, with edges slightly ruffled.
3. *Arrangement.*—Regular at all stages.
4. *Petaloids in center.*—Few, from 2–4.
5. *Persistence.*—Drop off cleanly.
6. *Fragrance.*—Strong, sweet and fruity.
7. *Lasting quality.*—Good; 9 to 13 days on plant; Good; 7 to 9 days in vase.

REPRODUCTIVE ORGANS

A. Stamen:

1. *Arrangement.*—Regularly arranged around styles.
2. *Number.*—112–118.

1 Drawing Sheet

3. *Length.*—6–18 mm.
4. *Filaments.*—Color — 155D, maturing to 55D.
5. *Anthers.*—Color — 164A.
6. *Pollen.*—25B.

B. Pistil:
1. *Styles.*—Smooth from base; color — close to 42A.
2. *Stigma.*—Color — close to 11B.
3. *Ovary.*—Pearshaped; 8 mm through center diameter.

C. Hips: Readily accepts own pollen; readily accepts foreign pollen.
1. *Shape.*—Rounded; to 2½ cm diameter, to 1½ cm depth.
2. *Color.*—When mature, near 167A.
3. *Seed.*—Average 10–15, frequently exposed.

PLANT

A. Form: Upright.

B. Growth: Vigorous; very high — average is 2.5 meters.

C. Foliage: Compound of 3 to 5 leaflets on bloom stem; 5 to 7 leaflets on main canes.
1. *Size.*—Very large.
2. *Quantity.*—Abundant.
3. *Color.*—New foliage has glossy finish. Upper side — 187A. Under side, 176B with green veining. Old foliage has matte finish. Upper side is 137A. Under side of old foliage is 147B.
4. *Shape.*—Ovate with acuminate apex.

5. *Texture.*—Upper side leathery.
6. *Edge.*—Slight serration on outer edge. Average points 4 per cm, with up to 1 mm peak.
7. *Rachis.*—Slight glandular hair on upper side; lower side occasional 2–3 hooked, 3–5 mm prickles about 1½ to 2 cm spacing.
8. *Stipules.*—Very narrow with long, slender auricle about 1.2 cm long.

D. Resistance to disease: When greenhouse grown, appears to be highly resistant to rust and blackspot. Fair resistance to mildew.

E. Frost tolerance: Unknown. Greenhouse environment only.

F. Resistance to insects: Susceptible to mild infestation of aphid and mites.

G. Wood:
*New wood.*—Color near 146B, Bark smooth.
*Old wood.*—Color near 138A, Bark smooth.

F. Prickles:
1. *Quantity.*—On Main canes — few.
2. *Form.*—Medium and straight.
3. *Color.*—On flowering stems, 166B.

I claim:

1. A new and distinct variety of rose plant of the hybrid tea class, substantially as described above and characterized by very fragrant, medium sized and prolific blooms of a pale lavender color, deepening in color with maturity and being borne singly on long, straight stems with matte foliage.

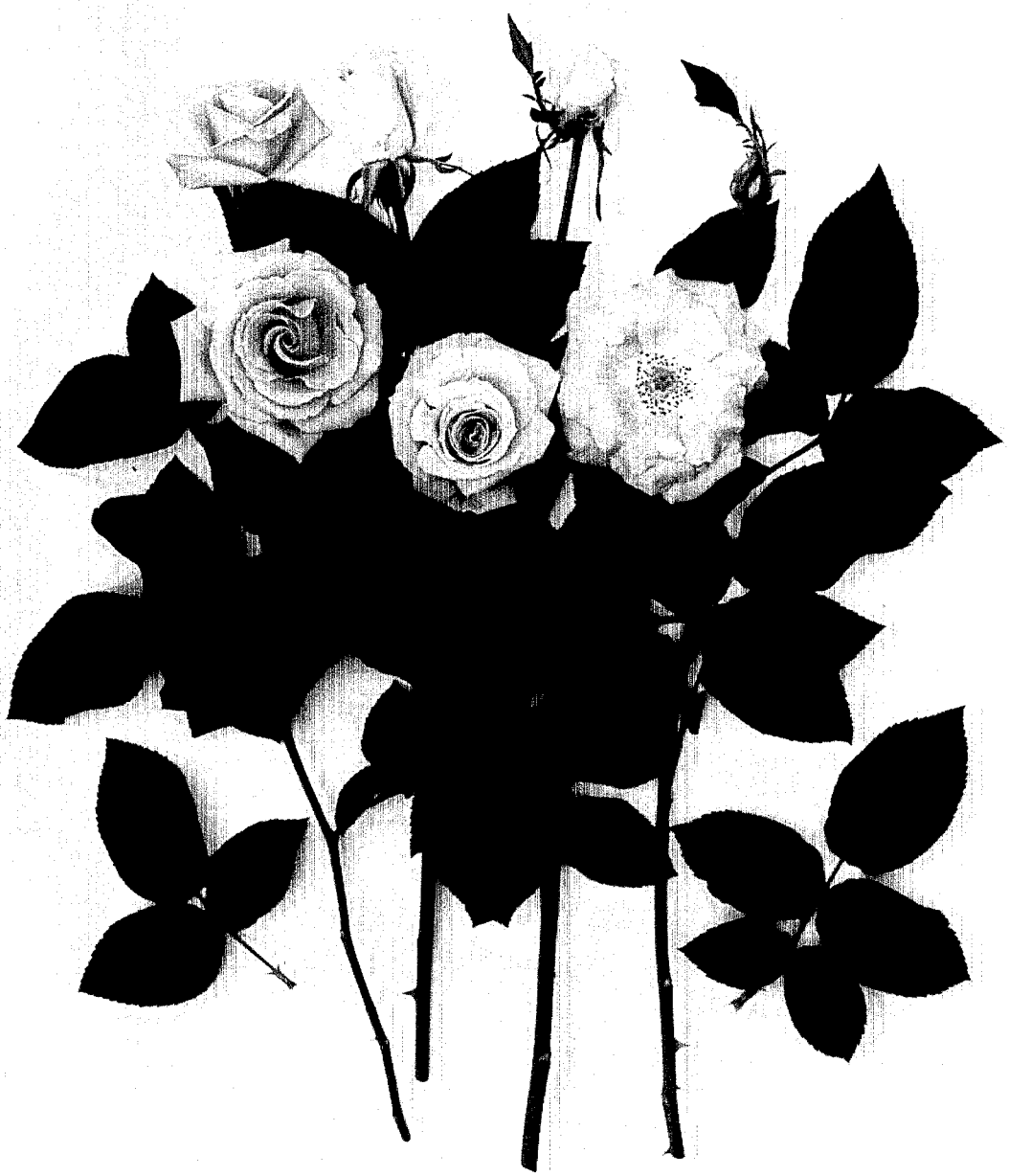

* * * * *